(12) United States Patent
Grimaud et al.

(10) Patent No.: US 8,962,869 B2
(45) Date of Patent: Feb. 24, 2015

(54) PROCESS FOR SYNTHESIZING KETO BENZOFURAN DERIVATIVES

(75) Inventors: Bernard Grimaud, Paris (FR); Pierre-Jean Grossi, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/006,027

(22) PCT Filed: Mar. 23, 2012

(86) PCT No.: PCT/FR2012/050607
§ 371 (c)(1),
(2), (4) Date: Sep. 18, 2013

(87) PCT Pub. No.: WO2012/127174
PCT Pub. Date: Sep. 27, 2012

(65) Prior Publication Data
US 2014/0046078 A1    Feb. 13, 2014

(30) Foreign Application Priority Data

Mar. 24, 2011 (FR) .................... 11 52453
Jun. 24, 2011 (FR) .................... 11 55610

(51) Int. Cl.
| | |
|---|---|
| *C07D 307/00* | (2006.01) |
| *C07D 307/80* | (2006.01) |
| *C07C 311/08* | (2006.01) |
| *C07C 311/21* | (2006.01) |
| *C07D 307/84* | (2006.01) |
| *C07D 307/83* | (2006.01) |

(52) U.S. Cl.
CPC ............ *C07D 307/80* (2013.01); *C07C 311/08* (2013.01); *C07C 311/21* (2013.01); *C07D 307/84* (2013.01); *C07D 307/83* (2013.01)
USPC ....................................... 549/468

(58) Field of Classification Search
USPC ....................................... 549/468
See application file for complete search history.

(56) References Cited

U.S. PATENT DOCUMENTS 5,223,510 A    6/1993   Gubin et al.

FOREIGN PATENT DOCUMENTS

| EP | 0 471 609 A1 | 2/1992 |
|---|---|---|
| WO | WO 02/48132 A1 | 6/2002 |
| WO | WO 2009/044143 A2 | 4/2009 |

OTHER PUBLICATIONS

Adams, R. et al., Quinone Imides. XXXIX. Adducts of Quinone Monoimides and Conversion of Active Methylene Adducts to Benzofurans, Journal of the American Chemical Society, (1956), vol. 78, No. 3, pp. 658-663.
International Search Report dated Jul. 5, 2012 issued in PCT/FR2012/050607, previously submitted on Sep. 18, 2013.

*Primary Examiner* — Noble Jarrell
*Assistant Examiner* — Raymond Covington
(74) *Attorney, Agent, or Firm* — Scully, Scott, Murphy & Presser P.C.

(57) ABSTRACT

The invention relates to a method for synthesizing benzofuran derivatives, in particular the dronedarone of formula (D), including carrying out a Fries rearrangement reaction using a sulfonamido-benzofuran ester intermediate.

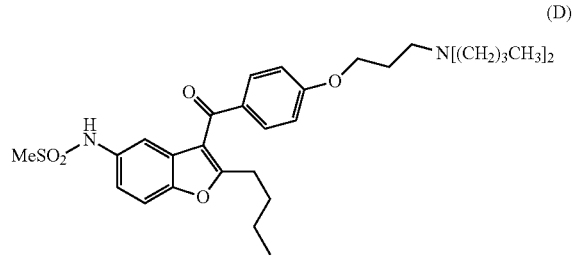

7 Claims, No Drawings

PROCESS FOR SYNTHESIZING KETO BENZOFURAN DERIVATIVES

The present invention relates to keto benzofuran derivatives of general formula (I) represented below, and also to a process for synthesizing them via coupling between a quinoneimine and a keto ester, and to synthetic intermediates thereof.

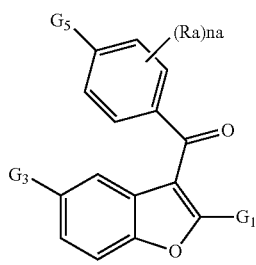

In the keto benzofuran derivatives of formula (I),

G1 represents a linear or branched alkyl (i), haloalkyl (ii), cycloalkyl (iii), substituted or unsubstituted aryl (iv), alkene (v) or alkyne (vi) group, G3 represents (i) a group —NHSO$_2$Rc or (ii) a group —NHRc, in which Rc represents (a) a linear or branched alkyl group, (b) a cycloalkyl group or (c) a substituted or unsubstituted aryl group, G5 represents a halogen atom or a group —ORb in which Rb represents a hydrogen atom, an alkyl, haloalkyl, aryl, arylalkyl, heteroaryl, cycloalkyl or heterocycloalkyl group or an -alkyleneaminoalkyl group, Ra is chosen from a hydrogen atom, halogen atoms and alkyl, haloalkyl, alkoxy and alkoxyalkyl groups, na is an index equal to 0, 1, 2, 3 or 4.

A particularly advantageous derivative of the keto benzofurans (I) is 2-n-butyl-3-[4-(3-di-n-butylaminopropoxy)benzoyl]-5-methylsulfonamidobenzofuran, known under the name dronedarone. Dronedarone, of formula (D) below:

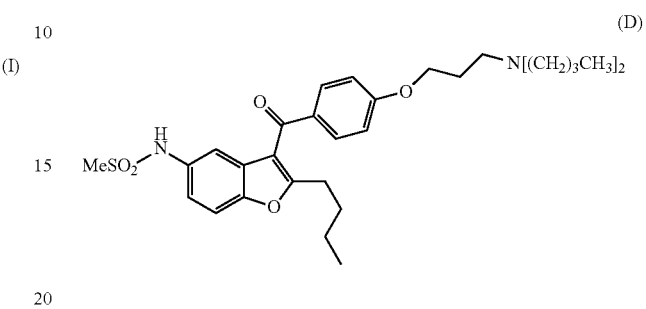

may be in the form of the free base or in salt form, in particular the hydrochloride salt of 2-n-butyl-3-[4-(3-di-n-butylaminopropoxy)benzoyl]-5-methylsulfonamidobenzofuran.

Dronedarone proves to be particularly useful as an active principle in indications of cardiac arrhythmia.

At the present time, dronedarone in free base form is synthesized according to the process described in EP 0 471 609 B1 via the key intermediate bearing a benzofuran nucleus, 2-butyl-5-nitrobenzofuran. In this synthetic process, the intermediate 2-butyl-5-nitrobenzofuran must be functionalized in position 3 and must be transformed in position 5, according to scheme 1 below. Specifically, the nitro group borne in position 5 of 2-butyl-5-nitrobenzofuran must be converted into methanesulfonamide by a reduction of —NO$_2$ to —NH$_2$ followed by a sulfonylation.

Scheme 1

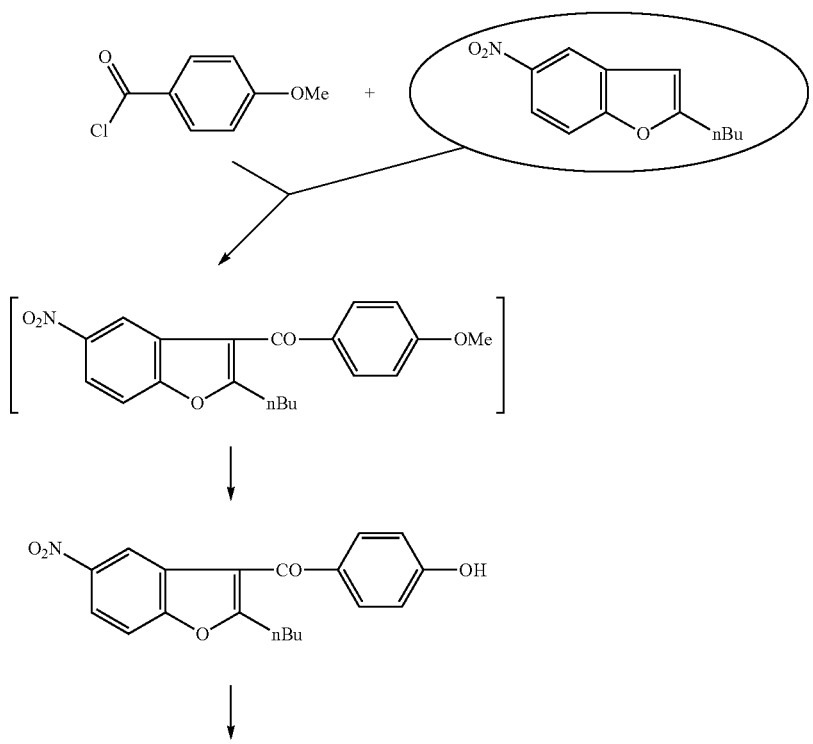

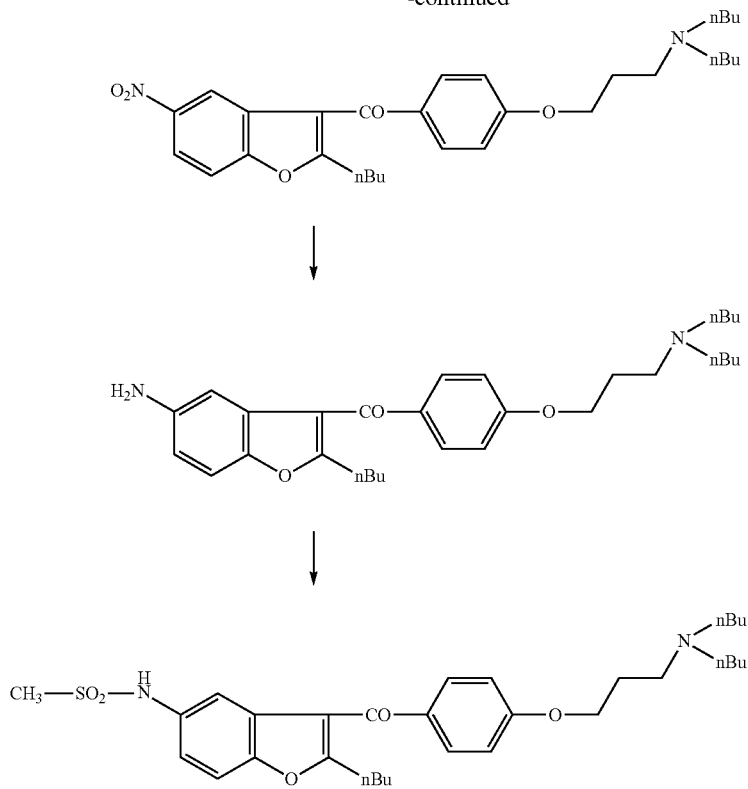

The complexity of the technical implementation of this type of process proves to be problematic and prejudicial in terms of yield, safety (use of hydrogen and of alkylating reagent during the mesylation) and of the environment (generation of iron or aluminum salts during the Friedel-Crafts step.

The Applicant thus sought novel synthetic routes using benzofurans, preferably already functionalized in positions 2, 3 and 5 of the benzofuran nucleus and advantageously already suitably functionalized in positions 2 and 5, in order to perform the synthesis of molecules of formula (I) above, thus making it possible to overcome the technical difficulties while at the same time optimally satisfying the cost, toxicity, safety and environmental friendliness constraints associated with the industrialization of such a synthetic process.

The Applicant has now found a novel process for synthesizing keto benzofuran derivatives of formula (I), in particular a novel process for synthesizing dronedarone of formula (D) above, comprising a step of Friedel-Crafts acylation or a Fries rearrangement reaction starting with a common intermediate. This process has the advantage of being able to synthesize the final molecule (I) from a common intermediate via two possible pathways which are referred to hereinbelow as route A and route B, affording a certain level of industrial flexibility.

According to a first aspect, the invention is directed toward a process for synthesizing a keto benzofuran derivative, in acid form (i), in base form (ii), in the form of an addition salt with an acid or a base (iii), in hydrate form (iv) or in solvate form (v), advantageously dronedarone or the hydrochloride salt thereof, said keto benzofuran derivative being of formula (I) below:

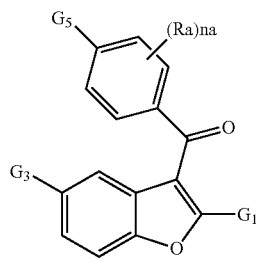

in which

G1 represents (i) a linear or branched alkyl group, advantageously a C1-C8 alkyl group and even more advantageously a C1-C4 alkyl group, for instance a methyl, ethyl, n-propyl, isopropyl, n-butyl, sec-butyl or tert-butyl group, (ii) a haloalkyl group, (iii) a cycloalkyl group, (iv) a substituted or unsubstituted aryl group, (v) an alkene group or (vi) an alkyne group, advantageously G1 represents an alkyl group and even more advantageously G1 represents an n-butyl group;

G3 represents (i) a group —NHSO$_2$Rc or (ii) a group —NHRc, in which Rc represents (a) a linear or branched alkyl group, advantageously a C1-C8 alkyl group and even more advantageously a C1-C4 alkyl group, for instance a methyl, ethyl, n-propyl, isopropyl, n-butyl, sec-butyl or tert-butyl group, (b) a cycloalkyl group or (c) a substituted or unsubstituted aryl group, advantageously G3 represents a group —NHSO$_2$alkyl or a group —NHSO$_2$aryl, and even more advantageously G3 represents a group —NHSO$_2$CH$_3$;

G5 represents a halogen atom or a group —ORb in which Rb represents a hydrogen atom, an alkyl, haloalkyl, aryl, arylalkyl, heteroaryl, cycloalkyl or heterocycloalkyl group or an -alkyleneaminoalkyl group, advantageously G5 represents a group —ORb with Rb chosen from -alkyleneaminoalkyl groups, advantageously Rb represents a 3-(di-n-butylamino)propyl group;

Ra represents a substituent chosen from a hydrogen atom, halogen atoms and alkyl, haloalkyl, alkoxy and alkoxyalkyl groups, advantageously Ra represents a substituent chosen from a hydrogen atom, halogen atoms and alkyl groups, na is an index equal to 0, 1, 2, 3 or 4, said process comprising (i) a Friedel-Crafts acylation reaction or (ii) a Fries rearrangement reaction, said reactions taking place starting with an intermediate of formula (II)

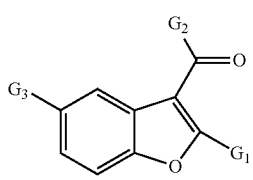
(II)

in which the groups G1 and G3 are as defined above and in which the group G2 is chosen from halogen atoms, the —OH group, alkoxy and aryloxy groups and —NRdRe with Rd and Re being identical or different and being chosen, independently of each other, from a hydrogen atom, alkyl groups and aryl groups, said alkyl and aryl groups being optionally substituted, advantageously G2 is chosen from halogen atoms, and even more advantageously G2 is chosen from chlorine and bromine, in the case where said intermediate (II) is engaged in a Friedel-Crafts reaction;

or from the following groups

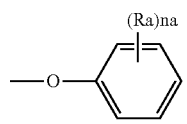

in which the phenyl is optionally substituted in the ortho and/or meta position, but never in the para position, with said radical Ra, with Ra and na as defined above, in the case where said intermediate (II) is engaged in a Fries reaction.

The compounds of formula (I) can comprise one or more asymmetric carbon atoms. They can therefore exist in the form of enantiomers or diastereoisomers. These enantiomers, diastereoisomers and also mixtures thereof, including racemic mixtures, form part of the invention.

The compounds of formula (I) may exist in the form of bases or of pharmaceutically acceptable addition salts with organic or mineral acids. Such addition salts form part of the invention. These salts may be prepared with pharmaceutically acceptable acids, but salts of other acids that are of use, for example, for purifying or isolating the compounds of formula (I) also form part of the invention.

According to another aspect, the invention also relates to synthetic intermediates such as the compounds of formulae (II), (VIII) and (IX), in base form, or in the form of pharmaceutically acceptable addition salts with organic or mineral acids, for example the salts defined above for formula (I), said compounds (II), (VIII) and (IX) having the following formula:

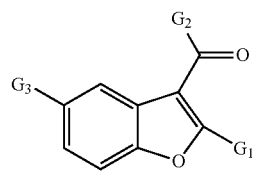
(II)

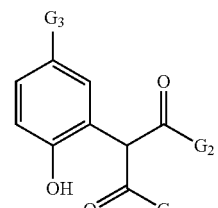
(VIII)

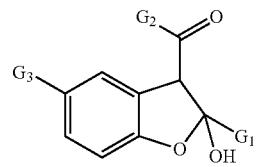
(IX)

in which G1 and G3 are as defined for the keto benzofuran of formula (I) above and in which the group G2 is chosen from halogen atoms, the —OH group, alkoxy and aryloxy groups and —NRdRe with Rd and Re being identical or different and being chosen, independently of each other, from a hydrogen atom, alkyl groups and aryl groups, said alkyl and aryl groups being optionally substituted, advantageously G2 is chosen from halogen atoms, and even more advantageously G2 is chosen from chlorine and bromine, or from the following groups

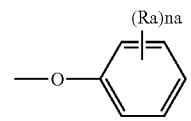

in which the phenyl is optionally substituted in the ortho and/or meta position, but never in the para position, with said radical Ra, with Ra and na as defined above for the keto benzofuran (I).

In the context of the present invention, and unless otherwise mentioned in the text, the following will be understood:

the numbering of the positions of the benzofuran nucleus is performed in the following manner:

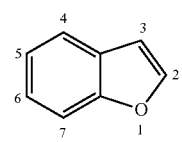

a halogen atom: a fluorine, chlorine, bromine or iodine atom;

an alkyl group: a saturated, linear or branched aliphatic group, which may comprise 1, 2, 3, 4 or 5 carbon atoms (abbreviated as —(C1-C5)alkyl). Examples that may be mentioned include (i) as —C1alkyl group, the methyl group, (ii) as —C2alkyl group, the ethyl group, (iii) as —C3alkyl group, the n-propyl group and the isopropyl group, (iv) as —C4alkyl group, the n-butyl group, the isobutyl group and the tert-butyl group, (v) as —C5alkyl group, the n-pentyl group and the isopentyl group;

a haloalkyl group: an alkyl group as defined above substituted with 1, 2, 3, 4 or 5 halogen atoms, as defined previously. Examples that will be mentioned are the -halo(C1-C5)alkyl groups, with (C1-C5)alkyl as defined above, for instance the trifluoromethyl group (abbreviated —$CF_3$) and the —$CH_2$—$CF_3$ group;

an alkylene group: a saturated, linear or branched, divalent alkyl group as defined previously, which may comprise 1, 2, 3, 4 or 5 carbon atoms (abbreviated —(C1-C5)alkylene-) or —$(CH_2)_{1 \text{ to } 5}$—. Examples that may be mentioned include methylene (or —$CH_2$—), ethylene (or —$CH_2$—$CH_2$—) and propylene (—$CH_2$—$CH_2$—$CH_2$— or —$C(CH_3)_2$—) radicals;

an alkoxy group: a radical —O-alkyl in which the alkyl group is as defined previously. Examples that may be mentioned include groups —O—(C1-C5)alkyl or —(C1-C5) alkoxy, and in particular (i) as group —O—C1alkyl, the group —Omethyl, (ii) as group —O—C2alkyl, the group —Oethyl, (iii) as group —O—C3alkyl, the group —Opropyl and the group —Oisopropyl, (iv) as group —O—C4alkyl, the group —Obutyl, the group —Oisobutyl and the group —Otert-butyl, (v) as group —O—C5alkyl, the group —Opentyl, the group —Oisopentyl and the group —Oneopentyl;

an aryloxy group: a radical —O-aryl in which the aryl group is as defined below;

an aryl group: a cyclic aromatic group comprising 6, 7, 8, 9 or 10 carbon atoms. Examples of aryl groups that may be mentioned include the phenyl group (abbreviated Ph), the naphthyl group, a —$C_6H_4$-alkyl group (with the alkyl radical, as defined previously, in the ortho, meta or para position on the aromatic nucleus). —$C_6H_4$-alkyl groups that may be mentioned include —$C_6H_4$—$CH_3$ groups with $CH_3$ in the ortho, meta or para position;

an arylalkyl group: an aryl group, as defined above, substituted with at least one alkyl group, as defined above. Advantageously, they are -alkylaryl radicals. An example that may be mentioned is the benzyl radical, i.e. the radical —$CH_2$-Ph;

an alkoxyalkyl group: a radical of formula -alkylene-O-alkyl, in which the alkyl and alkylene groups, comprising the same carbon number or not comprising the same carbon number, are as defined previously. Examples that may be mentioned include the groups —(C1-C5)alkylene-O—(C1-C5)alkyl, with —(C1-C5)alkylene- and —(C1-C5)alkyl as defined above;

an alkoxyaryl group: a radical of formula -alkylene-O-aryl, in which the aryl and alkylene groups, comprising the same carbon number or not comprising the same carbon number, are as defined previously. Examples that may be mentioned include the groups —(C1-C5)alkylene-O—(C1-C5)alkyl, with —(C1-C5)alkylene- and —(C1-C5)alkyl as defined above;

a heteroaryl group: a cyclic aromatic group comprising 2, 3, 4 or 5 carbon atoms and comprising 1, 2 or 3 heteroatoms, which may be chosen independently of each other, so as to be identical or different, when there are 2 of them, or independently of each other, so as to be identical or different, when there are 3 of them, from a nitrogen atom, an oxygen atom and a sulfur atom. Mention may be made of pyridyl, furanyl and pyrrolyl groups;

a cycloalkyl group: a cyclic alkyl group, which may comprise 3, 4, 5, or 6 carbon atoms, also abbreviated —(C3-C6) cycloalkyl. Examples that may be mentioned include cyclopropyl, cyclobutyl, cyclopentyl and cyclohexyl groups;

a heterocycloalkyl: an optionally bridged cyclic alkyl group comprising 5, 6 or 7 carbon atoms and comprising 1, 2 or 3 heteroatoms, which may be chosen, independently of each other, so as to be identical or different, when there are 2 of them, or independently of each other, so as to be identical or different, when there are 3 of them, from a nitrogen atom, an oxygen atom and a sulfur atom. Mention may be made especially of piperidyl, piperazinyl, pyrrolidinyl, hexamethyleneimino, morpholinyl and 1,1-dioxydotetrahydrothienyl groups;

an alkyleneaminoalkyl group: a group of formula -alkylene-N(alkyl)$_2$, in which the alkylene and alkyl groups, comprising the same carbon number or not comprising the same carbon number, are as defined previously. The two alkyl groups may comprise a different carbon number from each other. Examples that may be mentioned include the groups —(C1-C5)alkylene-N[(C1-C5)alkyl]$_2$, with —(C1-C5)alkylene- and —(C1-C5)alkyl as defined above. Advantageously, mention may be made of the —$(CH_2)_3N[(CH_2)_3CH_3]_2$ group;

an alkene group: a group of formula —$C_nH_{2n}$ in which n is a natural integer greater than or equal to 2, which may be linear or branched and which is characterized by the presence of at least one covalent double bond between two of its carbon atoms: mention may be made of the ethylene group and the 1,3-butadiene group;

an alkyne group: a group of formula $C_nH_{2n-2}$ in which n is a natural integer greater than or equal to 2, which may be linear or branched and which is characterized by the presence of at least one covalent triple bond between two of its carbon atoms. Mention may be made of an acetylene group, a 1-butyne group or a dimethylacetylene group.

leaving group, hereinbelow means a group which can be easily cleaved from a molecule by breaking a heterolytic bond, with loss of an electron pair. This group can thus be easily replaced with another group in a substitution reaction, for example. Such leaving groups are, for example, halogens or an activated hydroxyl group, such as a mesyl, tosyl, triflate, acetyl, etc. Examples of leaving groups and also the references for preparing them are given in *Advances in Organic Chemistry*, J. March, 3rd Edition, Wiley Interscience, pp. 310-316.

According to one embodiment, a subject of the invention is in particular a process for synthesizing a compound of formula (I) for which G3 is —NH—SO2-Rc, G5 is ORb, this compound is referred to as the keto sulfonamidobenzofuran derivative of formula (14) represented below,

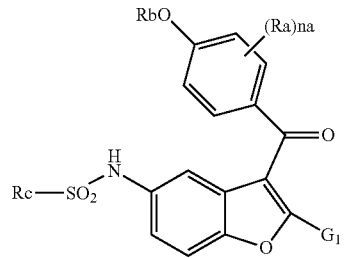

(14)

in which

G1 represents (i) a linear or branched alkyl group, advantageously a C1-C8 alkyl group and even more advantageously a C1-C4 alkyl group, for instance a methyl, ethyl, n-propyl, isopropyl, n-butyl, sec-butyl or tert-butyl group, (ii) a haloalkyl group, (iii) a cycloalkyl group, (iv) a substituted or unsubstituted aryl group, (v) an alkene group or (vi) an alkyne group, advantageously, G1 represents an alkyl group and even more advantageously G1 represents a methyl or n-butyl group;

and/or

Ra represents a substituent chosen from a hydrogen atom, halogen atoms and alkyl, haloalkyl, alkoxy and alkoxyalkyl groups, advantageously Ra represents a substituent chosen from a hydrogen atom, halogen atoms and alkyl groups, and even more advantageously Ra represents a hydrogen atom, and/or na is equal to 0, 1, 2, 3 or 4, and advantageously na is equal to 0, 1 or 4, and/or Rb represents a hydrogen atom, an alkyl, haloalkyl, aryl, arylalkyl, heteroaryl, cycloalkyl or heterocycloalkyl group or an -alkyleneaminoalkyl group, advantageously Rb is chosen from -alkyleneaminoalkyl groups, and even more advantageously Rb represents a 3-(di-n-butylamino)propyl group;

and/or

Rc represents (a) a linear or branched alkyl group, advantageously a C1-C8 alkyl group and even more advantageously a C1-C4 alkyl group, for instance a methyl, ethyl, n-propyl, isopropyl, n-butyl, sec-butyl or tert-butyl group, (b) a cycloalkyl group or (c) a substituted or unsubstituted aryl group, advantageously Rc represents an alkyl group or an aryl group, and even more advantageously Rc represents a —CH$_3$ group;

said process comprising (i) a Friedel-Crafts acylation reaction or (ii) a Fries rearrangement reaction, said reactions taking place starting with the sulfonamidobenzofuran intermediate of formula (III), i.e. a compound of formula (II) for which G3 represents —NH—SO$_2$-Rc,

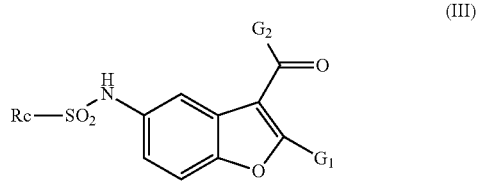

(III)

in which G1 and Rc are as defined above and the group G2 is chosen from halogen atoms, the —OH group, alkoxy and aryloxy groups and —NRdRe with Rd and Re being identical or different and being chosen, independently of each other, from a hydrogen atom, alkyl groups and aryl groups, said alkyl and aryl groups being optionally substituted, advantageously G2 is chosen from halogen atoms, and even more advantageously G2 is chosen from chlorine and bromine, in the case where said intermediate (II) is engaged in a Friedel-Crafts reaction;

or from the following groups

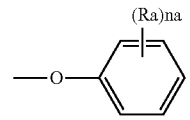

in which the phenyl is optionally substituted in the ortho and/or meta position, but never in the para position, with said radical Ra, with Ra and na as defined above, in the case where said intermediate (II) is engaged in a Fries reaction.

According to one embodiment, the group G2 in the intermediate of formula (II) or (Ill) is chosen from —OH, optionally substituted —Ophenyl, chlorine and bromine.

According to one embodiment, said keto sulfonamidobenzofuran derivative of formula (14) contains a radical Ra which is a hydrogen atom, an na which is equal to 4, a radical Rc which is a methyl or phenyl group, a radical G1 which is an n-butyl group and/or a radical Rb which is a —(CH$_2$)$_3$N[(CH$_2$)$_3$CH$_3$]$_2$ group or a —(CH$_2$)$_3$N$^+$H[(CH$_2$)$_3$CH$_3$]$_2$, Cl$^-$ group.

According to one embodiment, said keto sulfonamidobenzofuran derivative of formula (14) is dronedarone of formula (D) in free base or salt form, advantageously in hydrochloride form.

The first part of the synthesis according to the invention, as represented in scheme 2 below, consists of an oxidation reaction of a phenolic derivative (V) to a p-quinone derivative (VI) in which G4 is chosen from (i) groups =NSO$_2$alkyl, (ii) groups =NSO$_2$aryl and (iii) groups =NRc in which Rc is chosen from hydrogen, alkyl or aryl groups and haloalkyl groups, advantageously the group G4 represents a group =NSO$_2$alkyl, even more advantageously the group G4 represents a group =NSO$_2$CH$_3$.

Oxidizing agents for this oxidation reaction in accordance with the invention that may be mentioned include:

sodium or potassium dichromate, (K$_2$Cr$_2$O$_7$, Na$_2$Cr$_2$O$_7$),
activated manganese dioxide, (MnO$_2$)
iodylbenzene (C$_6$H$_5$IO$_2$),
iodosylbenzene (C$_6$H$_5$IO), and
lead tetraacetate, (Pb(OAc)$_4$),
chromate-based reagents, such as Collins' reagents, Jones' reagent, Ag$_2$O, peroxides such as dicumyl peroxide, cumene hydroperoxide, etc.; DMSO, DDQ (dichlorodicyanoquinone), peracids such as chloroperbenzoic acid, other perbenzoic acids; hypervalent iodine reagents (Ph-I(OAc)$_2$, etc.), hydrogen peroxide, oxygen (air), bleach, supported oxidizing agents, electrolytic processes,
in, for example, solvents such as glacial acetic acid, ethyl acetate, acetone, acetonitrile, pyridine, chlorinated solvents such as chlorobenzene or dichloromethane, aromatic solvents such as benzene, linear or cyclic alkanes, water, DMSO, DMAP, and carboxylic acids such as acetic acid.

Examples that may thus be mentioned include:
an oxidation reaction with sodium dichromate monohydrate in 20% sulfuric acid for about 1 hour at room temperature, or
an oxidation reaction with about 0.333 equivalent of potassium dichromate and about 1.333 equivalents of sulfuric acid per approximately 1 equivalent of phenolic derivative, an oxidation reaction with an acetic acid solution containing about 0.5 equivalent of potassium dichromate per approximately 1 equivalent of phenolic derivative, an oxidation reaction performed with heating with 1 to 4 equivalents, for example about 1 or 4 equivalents of activated $MnO_2$ (relative to the aminophenol engaged) in benzene, or an oxidation reaction, which is performed over a few tens of minutes, with a large excess of $MnO_2$ (about 7 equivalents and more) in dichloromethane or acetonitrile at room temperature, an oxidation reaction with iodylbenzene ($C_6H_5IO_2$), the reactivity of which is increased by catalysis with a Lewis acid (for example: vanadyl acetylacetonate) in refluxing benzene or toluene for about 4 hours. Iodylbenzene is not commercially available, and needs to be synthesized beforehand from iodobenzene. Several synthetic processes are described mainly using sodium hypochlorite in acetic acid.

an oxidation reaction in the presence of about 2.5 equivalents of iodosylbenzene ($C_6H_5IO$) in methanol over a molecular sieve (4 Å) for about 1 hour of stirring at about 0° C.

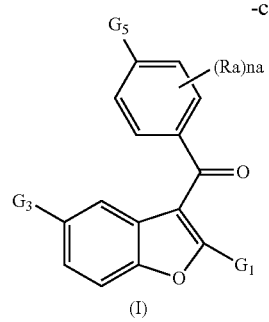

(I)

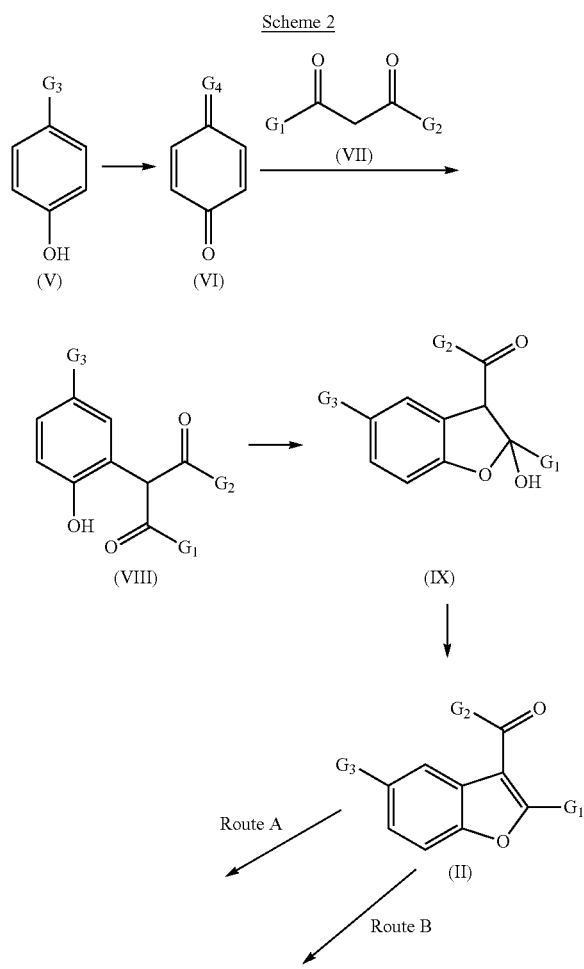

Sodium and potassium dichromates are common reagents that are less expensive and less toxic than lead tetraacetate.

The oxidation reaction that appears to be the most advantageous is obtained with $MnO_2$ in acetic acid. From the start, the reaction is complete with this oxidizing agent. In addition, the low toxicity of $MnO_2$, compared with that of $Pb(OAc)_4$, is reduced.

Advantageously, the oxidation reaction of the phenolic derivative (V) to the p-quinone derivative (VI) is performed with $K_2Cr_2O_7$ or $MnO_2$ as oxidizing agent in acetic acid.

Next, a coupling reaction of said quinoneimine derivative (VI) with a dicarbonyl derivative (VII) takes place, in the presence of a base, for instance a strong base such as, for example, an alkoxide. This reaction may take place, for example, in an aprotic solvent such as DMF or dioxane at room temperature.

The dicarbonyl derivative (VIII) is then engaged in a cyclization reaction to give a benzodihydrofuran derivative (IX), which, by dehydration, will then lead to the aromatic benzofuran derivative (II). This reaction may take place, for example, in an aprotic solvent such as DMF or dioxane. The cyclization/dehydration may take place in strong acid medium, for example using hot hydrochloric acid for 3 hours.

The groups G1, G2 and/or G3 of compounds (V), (VII), (VIII), (IX) and (II) of scheme 3 above are as defined for the keto benzofuran of formula (I) in accordance with the invention.

The keto benzofuran derivative (I) is then obtained from said aromatic benzofuran intermediate derivative (II) either via a Friedel-Crafts acylation route A or via a Fries rearrangement route B.

According to one embodiment, the first part of the synthesis according to the invention, as represented in scheme 3 below, consists in synthesizing an intermediate (7). Said intermediate is the sulfonamidobenzofuran ester of formula (7) below:

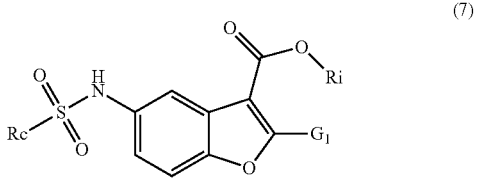

in which Rc and G1 are as defined above and Ri represents a hydrogen atom, an alkyl or an aryl, and is advantageously a methyl, an ethyl or a phenyl. This intermediate (7) may thus be obtained after the following successive steps, represented in scheme 3:

Sulfonylation of the p-aminophenol of formula (1);
Oxidation of the p-aminosulfonylphenol (2) obtained in the preceding step to the p-quinone sulfonimide of formula (3), i.e. a compound of formula (VI) for which G4 represents =N—$SO_2$-Rc;

Coupling of said p-quinone sulfonimide of formula (3) with a β-keto ester of formula (4), i.e. a compound of formula (VII) for which G2 represents —ORi;

Cyclization of the sulfonamido keto ester benzofuran (5), i.e. a compound of formula (VIII) for which G2 represents —ORi and G3 represents —NH—SO$_2$-Rc, leading to the formation of the sulfonamido-hydroxybenzofuran (6), i.e. a compound of formula (IX) for which G2 represents —ORi and G3 represents —NH—SO$_2$-Rc;

Dehydration/aromatization of the sulfonamido-hydroxybenzofuran (6) allowing the formation of the benzofuran aromatic nucleus of the sulfonamidobenzofuran ester of formula (7).

Scheme 3

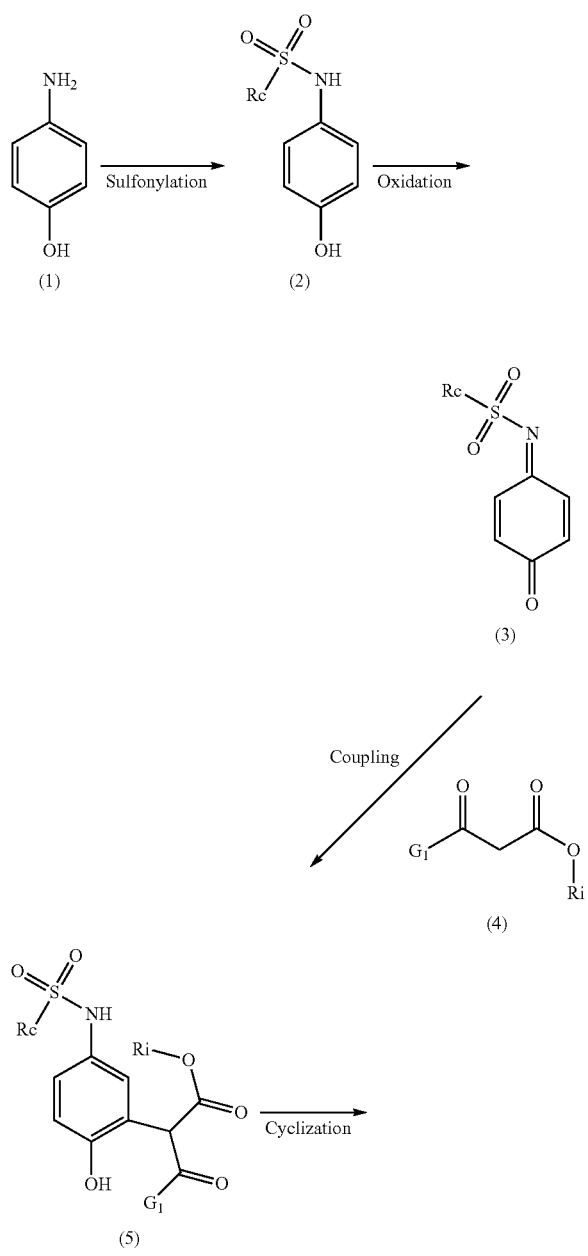

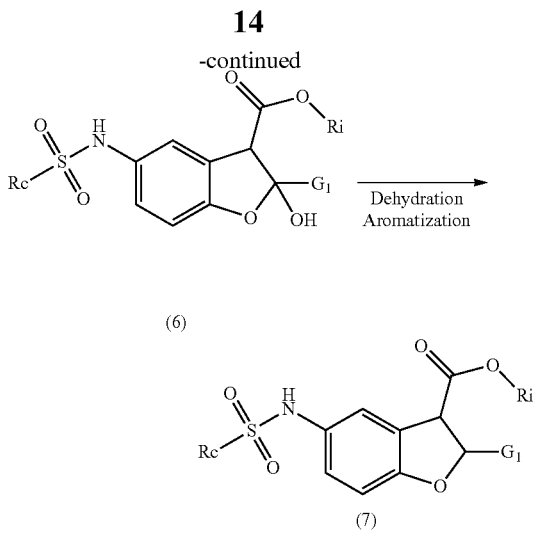

The groups G1 and/or Rc of compounds (2), (3), (4), (5), (6) and (7) of scheme 3 above are as defined for the keto benzofuran of formula (I) according to the invention and Ri is as defined for compound (7) above.

The sulfonylation reaction of the p-aminophenol (1) to the p-sulfonamidophenol (2) may be performed using RcS(O)$_2$Cl, with Rc as defined above, in the presence of a base. Document J. Am. Chem. Soc, 1951, 73, 1145-1149 by R. Adams and J. H. Looker describes the operating conditions enabling such a sulfonylation and oxidation.

In the case where Rc═CH$_3$, it is p-methanesulfonamidophenol obtained from the p-aminophenol (1) mesylated with methanesulfonyl chloride in the presence of a base. In the case where Rc═C$_6$H$_5$, it is p-benzenesulfonamidophenol obtained from the p-aminophenol (1) sulfonylated with benzenesulfonyl chloride in the presence of a base.

The reaction solvent may be chosen, for example, from methanol, ethanol, pyridine, dimethylformamide (abbreviated DMF), dichloromethane, chloroform, chlorobenzene, dichloroethane, benzene, toluene, ethyl acetate, acetonitrile, acetone, tetrahydrofuran (abbreviated THF), dioxane and N-methylpyrrolidinone, and advantageously it is chosen from pyridine, methanol, DMF and N-methylpyrrolidinone.

The base may be chosen, for example, from pyridine, triethylamine, hydrogen carbonates, potassium carbonate, sodium carbonate, sodium hydroxide and ammonia, and advantageously potassium or sodium carbonate.

The reaction is preferably performed at a temperature below room temperature.

According to one embodiment, RcS(O)$_2$Cl is methanesulfonyl chloride or benzenesulfonyl chloride.

This sulfonylation reaction may advantageously be performed with 1 equivalent of methanesulfonyl chloride poured between 10° C. and 15° C. onto 2 equivalents of p-aminophenol suspended in slightly more than 11 volumes of methanol (volume in ml/weight in g of p-aminophenol). The second equivalent of p-aminophenol serves to take up the acid formed, the amine function acting as a base.

It may also take place in methanol by adding an equivalent of methanesulfonyl chloride and by slowly neutralizing up to pH=6 with NaHCO$_3$.

The p-sulfonamidophenol (2) then undergoes an oxidation reaction leading to the formation of p-quinone monoimide (3): when Rc═CH$_3$, it is p-methanesulfonamidophenol and when Rc═C$_6$H$_5$, it is p-benzenesulfonamidophenol.

This oxidation reaction may be performed, for example, using:
(i) lead tetraacetate, advantageously using lead tetraacetate in acetic acid,
(ii) sodium or potassium dichromate (or $K_2Cr_2O_7$), advantageously using sodium dichromate monohydrate in sulfuric acid or acetic acid,
(iii) activated manganese dioxide, advantageously $MnO_2$ in glacial acetic acid, ethyl acetate, acetone, acetonitrile, pyridine, chlorinated solvents such as chlorobenzene or dichloromethane, aromatic solvents such as benzene, linear or cyclic alkanes, water, DMSO, DMAP, and carboxylic acids such as acetic acid.
or
(iv) iodylbenzene ($C_6H_5IO_2$) or iodosylbenzene ($C_6H_5IO$), advantageously iodylbenzene ($C_6H_5IO_2$) in the presence of a Lewis acid, for instance vanadyl acetylacetonate, in benzene or toluene.

According to one embodiment, sodium or potassium dichromate, advantageously $K_2Cr_2O_7$ in acetic acid, or activated manganese dioxide are used.

The p-quinone monoimide (3) then undergoes a coupling reaction with:
the keto ester of formula (4) with G1 and Ri as defined above;
advantageously, it is ethyl acetoacetate or methyl 3-oxoheptanoate,
advantageously in the presence of a base.

Dioxane or acetone may be mentioned as suitable solvent for this coupling reaction. Alkoxides such as, for example, sodium methoxide, lithium methoxide, sodium ethoxide and lithium ethoxide may be mentioned as suitable base.

When G1=n-butyl and Ri=methyl or phenyl, the keto ester (4) is then methyl or phenyl 3-oxoheptanoate, which, by coupling reaction with p-methanesulfonamidophenol, gives directly methyl or phenyl 2-n-butyl-5-methanesulfonamidobenzofuran-3-carboxylate.

Specifically, the substituted aminophenol resulting from the preceding coupling, of formula (5), is then cyclized in acidic medium, advantageously in the presence of hydrochloric acid, phosphoric acid, sulfuric acid, methanesulfonic acid, trifluoroacetic acid or acetic anhydride, leading, after dehydration and aromatization, to the sulfonamidobenzofuran ester (7).

The second part of the synthesis may be performed using the sulfonamidobenzofuran ester intermediate (7) via two possible routes: route A comprising a Friedel-Crafts acylation step or route B comprising a Fries rearrangement step, represented in scheme 4 below, both leading to the formation of the keto benzofuran (14) in accordance with the invention.

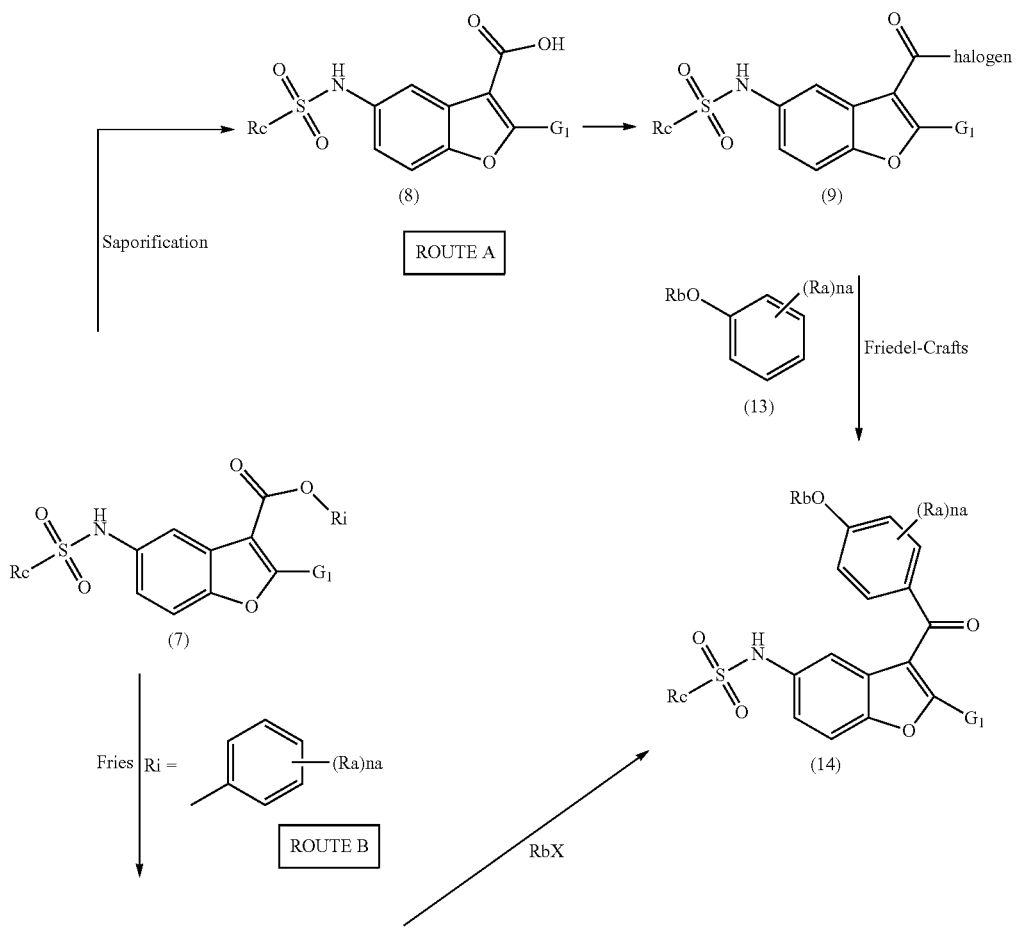

Scheme 4

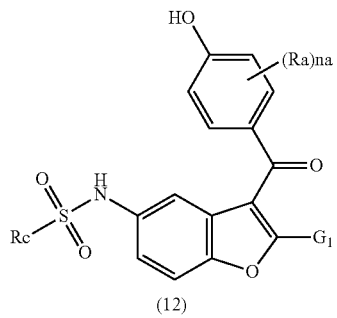

(12)

Route A: Friedel-Crafts Acylation

According to one embodiment, the synthetic process according to the invention is characterized in that the sulfonamidobenzofuran ester of formula (7) is engaged in a Friedel-Crafts route A as represented above in scheme 4, successively comprising a step:

- of saponification of the ester function of the sulfonamidobenzofuran ester of formula (7), leading to the formation of the sulfonamidobenzofuran acid (8);
- of formation of a sulfonamidobenzofuran acyl halide of formula (9), advantageously the sulfonamidobenzofuran acyl bromide of formula (9') or the sulfonamidobenzofuran acyl chloride of formula (9'') from said sulfonamidobenzofuran acid (8);
- of Friedel-Crafts acylation of the aromatic ether (13) with Rb, Ra and na as defined above, with said sulfonamidobenzofuran acyl halide of formula (9), in particular the sulfonamidobenzofuran acyl bromide of formula (9') or the sulfonamidobenzofuran acyl chloride of formula (9''), leading to the formation of said keto sulfonamidobenzofuran derivative of formula (14) according to the invention.

In the case of route A, the sulfonamidobenzofuran ester intermediate (7) bearing in position 3 an ester function is saponified with, for example, 10 weight % sodium hydroxide, giving the sulfonamidobenzofuran acid of formula (8) or the sodium salt thereof represented in scheme 4. This sulfonamidobenzofuran acid of formula (8) is then activated so as to be able to be engaged with the aromatic ether intermediate (13) in a Friedel-Crafts acylation reaction.

This activation consists in transforming the sulfonamidobenzofuran acid of formula (8) into a sulfonamidobenzofuran acyl halide of formula (9), advantageously the sulfonamidobenzofuran acyl bromide of formula (9') and the sulfonamidobenzofuran acyl chloride of formula (9'').

According to one embodiment, the sulfonamidobenzofuran acid of formula (8) is transformed into the sulfonamidobenzofuran acyl chloride of formula (9'') by reaction with thionyl chloride or oxalyl chloride.

According to another embodiment, the sulfonamidobenzofuran acid of formula (8) is transformed into the sulfonamidobenzofuran acyl bromide of formula (9') by reaction with thionyl bromide or oxalyl bromide.

Another possibility is to perform the Friedel-Crafts reaction with a compound of formula PhOR' (R'=alkyl or a leaving group). In this case, starting with the compound of formula (9), a compound of formula (14) is obtained, with Rb=R' which may be, for example, a methyl group. If Rb=R'=H, the compound of formula (12) is obtained directly.

Aromatic ether compounds that may advantageously be mentioned include phenol (Rb=H) (13), N,N-diethyl-N-(2-phenoxyethyl)amine in free base form, in hydrochloride form or any other salt of this amine, N,N-di-n-butyl-N-(2-phenoxypropyl)amine in free base form, in hydrochloride form or any other salt of this amine, phenol, and alkoxybenzenes (anisole, ethoxybenzene, ROPh with R being resistant in acidic medium and labile in basic medium, etc.).

The aromatic ether (13) may be obtained by reacting (i) phenol with (ii) a compound RbX in which Rb is as defined above and X is a leaving group, advantageously a halogen, better still a chloride or a bromide, (iii) in the presence of a base, for instance sodium hydroxide, and then by transforming the aromatic ether (13) obtained into a salt, advantageously into the hydrochloride salt. Advantageously, RbX is a tertiary amine halide, and even more advantageously RbX is Cl—$(CH_2)_3$N[$(CH_2)_3CH_3$]$_2$ or Br—$(CH_2)_3$N[$(CH_2)_3CH_3$]$_2$.

According to one embodiment, the coupling of the phenol takes place with N-(3-chloropropyl)-N,N-dibutylamine, giving N,N-dibutyl-N-(3-phenoxypropyl)amine. According to one embodiment, N,N-dibutyl-N-(3-phenoxypropyl)amine is salified to N,N-dibutyl-N-(3-phenoxypropyl)amine hydrochloride.

The Friedel-Crafts acylation of the aromatic ether compound (13), in free base or hydrochloride form, with the acylsulfonamidobenzofuran halide of formula (9) is catalyzed with a Lewis acid.

Examples of Lewis acids that may be mentioned include $SnCl_4$, $AlCl_3$, $FeCl_3$, $TiCl_4$, $BF_3$ and $Tf_2O$ (triflic anhydride).

According to one embodiment, the Friedel-Crafts acylation reaction of the aromatic ether compound (13) in free base form takes place in the presence of $SnCl_4$ as Lewis acid.

According to another embodiment, the Friedel-Crafts acylation reaction of the aromatic ether compound (13) in hydrochloride form takes place in the presence of $AlCl_3$ as Lewis acid.

The Friedel-Crafts acylation reaction may be conducted in a solvent of the type such as dichloromethane, chlorobenzene, nitrobenzene, toluene or xylene.

This reaction leads to the production of the keto sulfonamidobenzofuran (14), advantageously said keto sulfonamidobenzofuran in free base form in which Rc=—CH$_3$, G1=-nBu, Ra=H, na=4 and Rb=—C$_3$H$_6$N(Bu)$_2$, and even more advantageously the keto sulfonamidobenzofuran in hydrochloride form in which Rc=—CH$_3$, G1=-nBu, Ra=H, na=4 and Rb=—C$_3$H$_6$N$^+$(Bu)$_2$.

The Friedel-Crafts acylation reaction has the advantage of deactivating the aromatic nucleus engaged in this reaction, thus preventing multiple acylations.

According to a particularly advantageous embodiment represented in scheme 5 below, the Friedel-Crafts acylation takes place with (i) the acylsulfonamidobenzofuran halide of formula (9d), in particular the acylsulfonamidobenzofuran bromide of formula (9d) with halogen=Br or the acylsulfonamidobenzofuran chloride of formula (9d) with halogen=Cl, and (ii) with N,N-dibutyl-N-(3-phenoxypropyl)amine hydrochloride of formula (16d), which is itself obtained by reacting phenol (15) with N-(3-chloropropyl)-N,N-dibutylamine in the presence of sodium hydroxide in water, said acylation reaction leading to the formation of dronedarone of formula (D) according to the invention, which, at the end of the Friedel-Crafts reaction, may be isolated directly in hydrochloride form or may be isolated in base form and may subsequently be readily converted into pharmaceutically acceptable salts by addition to organic or mineral acids as defined above, in particular into hydrochloride salts by reaction with 36% hydrochloric acid at a temperature below 50° C.

However, the synthesis of keto sulfonamidobenzofuran derivatives of formula (I) according to the invention, and in particular of keto sulfonamidobenzofuran derivatives of formula (14), such as dronedarone of formula (D), may also take place via a Fries rearrangement according to route B described below.

Route B: Fries Rearrangement

According to one embodiment, the synthetic process according to the invention is characterized in that the sulfonamidobenzofuran ester of formula (5) is engaged in a Fries route B as represented above in scheme 4, successively comprising a step:

of Fries rearrangement of the sulfonamidobenzofuran ester of formula (7) for which Ri is a phenyl group, optionally substituted in the ortho and/or meta position but never in the para position, with a group Ra chosen from halogen atoms and alkyl, haloalkyl, alkoxy and alkoxyalkyl groups, into the keto sulfonamidobenzofuran of formula (12);

of coupling of the keto sulfonamidobenzofuran of formula (12) with a compound RbX as defined above, advantageously an amino halide RbX, leading to the keto sulfonamidobenzofuran derivative of formula (14).

Scheme 5

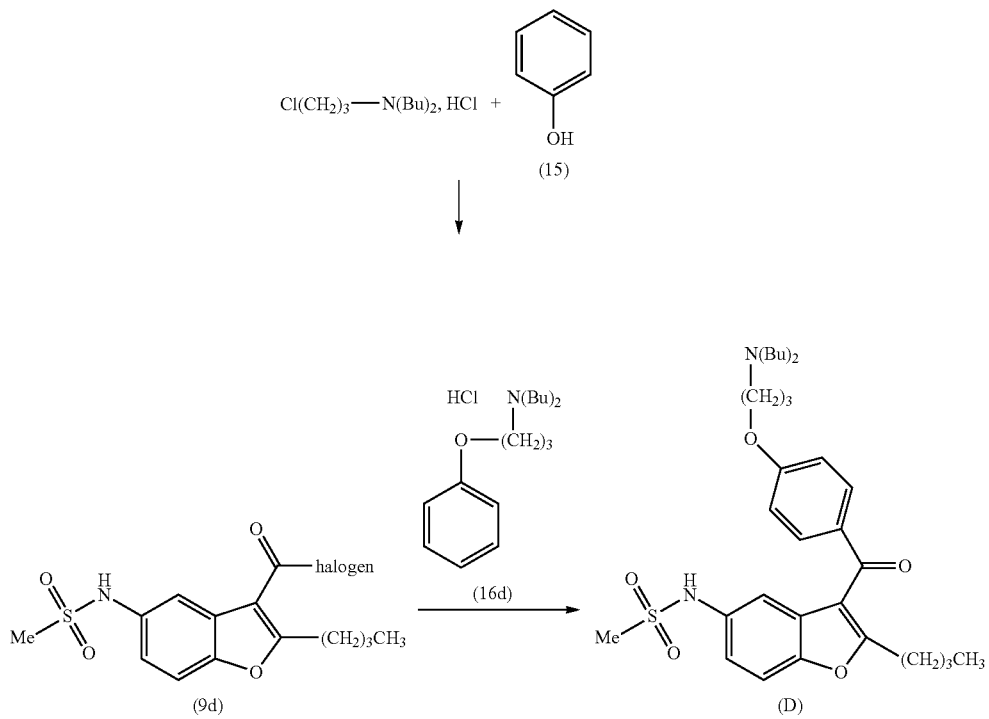

Scheme 6

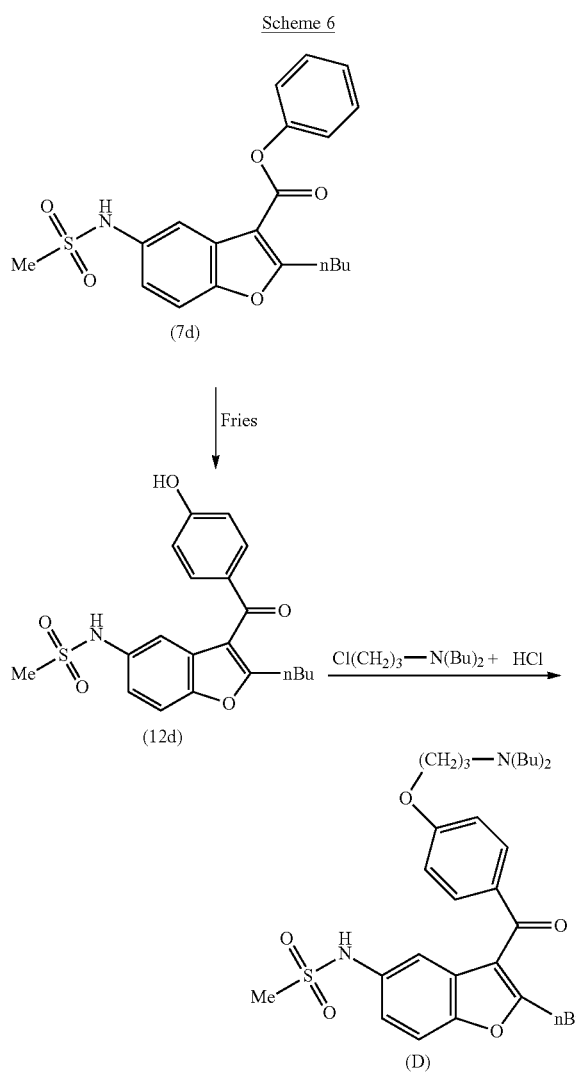

According to a particularly advantageous embodiment represented in scheme 6 above, the Fries reaction takes place with the intermediate of formula (7d) for which G1 represents an n-butyl group, leading to the formation of compound (12d), which, after nucleophilic substitution with Cl(CH$_2$)$_3$N(Bu)$_2$, results in the formation of dronedarone of formula (D). Dronedarone may then be readily converted into pharmaceutically acceptable salts by addition to organic or mineral acids as defined above, in particular into hydrochloride salts by reaction with 36% hydrochloric acid at a temperature below 50° C.

The Fries reaction may take place, for example, in a solvent such as chlorobenzene with 4 equivalents of aluminum chloride AlCl$_3$ at a temperature of about 90-95° C. for 13 to 17 hours.

The process according to the invention in particular has the following advantages:
  convergent synthesis;
  limited number of synthetic steps;
  possibility of performing in sequence several steps not requiring the isolation of the products obtained;
  reactions that are simple and technologically easy to perform;
  no hydrogenation step to obtain an amino function in position 5 of the benzofuran;
  common, readily available and inexpensive starting materials and reagents.

The invention will now be described in greater detail.

EXAMPLES

The procedures and examples below describe the preparation of the dronedarone intermediate. These procedures and examples are not limiting and merely serve to illustrate the present invention.

In the procedures and examples below:
  the NMR (nuclear magnetic resonance) spectra are acquired on a Fourier transform spectrometer (Brüker) at 300 MHz (exchangeable protons not recorded);
  s=singlet,
  d=doublet,
  m=multiplet,
  br=broad signal,
  t=triplet,
  q=quartet,
  DMSO-d$_6$=deuterated dimethyl sulfoxide.
  CDCl$_3$=deuterated chloroform.
  The solvent mixtures are quantified in volumetric ratios.
  The NMR spectra and mass spectra confirm the structures of the compounds obtained according to the examples below.
  The retention times by HPLC analysis are in minutes.
The HPLC conditions used are as follows:
  Column: Xterra RP18 3.5 μm, 100 mm*4.6 mm.
  mobile phase:
  A—0.01M KH$_2$PO$_4$ buffer
  B—Acetonitrile
  Flow rate: 1.0 ml/min.
  Gradient:

| Time (min) | % A | % B |
|---|---|---|
| 0 | 80 | 20 |
| 15 | 25 | 75 |
| 25 | 25 | 75 |
| 27 | 80 | 20 |
| 37 | 80 | 20 |

Detector: UV at 226 nm
Injection: 10 μl of product in dioxane/H$_2$O (95/5)
Retention:
Product Retention Times
2.6 min p-methanesulfonamidophenol
3.4 min p-quinone monomethanesulfonimide
10.6 min dronedarone HCl
11.3 min 2-butyl-5-(methanesulfonamido)benzofuran-3-carbonyl chloride
In the examples that follow, the following abbreviations are used:
h: hours
min: minutes
Eq: equivalent
DMF: N,N-dimethylformamide
MTBE: methyl tert-butyl ether
DCE: dichloroethane
DCM: dichloromethane
DMSO: dimethyl sulfoxide
RT: room temperature (between 20 and 25° C.)
m.p.: melting point
Yld: yield
HCl: hydrochloric acid
Lit.: literature In the general synthetic schemes which follow, the starting compounds and the reagents, when the method for preparing them is not described, are commercially available or described in the literature, or else can be prepared according to methods which are described therein or which are known to those skilled in the art.

Example 1

Synthesis of p-methanesulfonamidophenol (or N-(4-hydroxyphenyl)methanesulfonamide) According to Method I

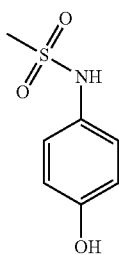

5.4 g (49.5 mmol) of p-aminophenol are dissolved in 40 ml of anhydrous pyridine, and 5.7 g (1 equivalent) of methanesulfonyl chloride diluted in 12 ml of pyridine are added over 15 minutes at 20° C. under a stream of nitrogen. The reaction medium is stirred for 3 days at 20° C. and is then poured into 1.5 liters of water containing a sufficient amount of hydrochloric acid (67 g of 36% HCl) to neutralize the pyridine and to establish a pH≤1.5. The aqueous phase is separated out by settling and extracted twice with 250 ml of ethyl acetate. The organic phases are combined and washed with twice 250 ml of water and then concentrated under vacuum. The residue is recrystallized from 40 ml of ethyl acetate. The crystals are filtered off at 0° C. and washed with 15 ml of ethyl acetate. 2.14 g of crude p-methanesulfonamidophenol are obtained.
Mass yield: 23% by weight
m.p.: 156.5° C. (lit. 154.5-155.5° C.)
$^1$H NMR (DMSO) δ 3.08 (s, 3H, CH$_3$S), 6.74 (d, 2H, CH$_{arom}$), 7.02 (d, 2H, CH$_{arom}$), 9.26 (broad s, 2H, OH and NH); $^{13}$C NMR (DMSO) δ 38.3 (1-CH$_3$), 115.5, 124.0 (4-CH$_{arom}$), 129.0 (1-C$_{arom}$—N), 154.8 (1-C$_{arom}$—O).

Synthesis of p-methanesulfonamidophenol (or N-(4-hydroxyphenyl)methanesulfonamide) According to Method II

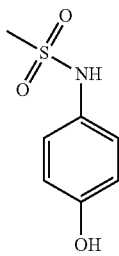

10 g (91.6 mmol) of p-aminophenol are dissolved in 250 ml of methanol supplemented with 0.5 ml of 36% hydrochloric acid. The mixture is stirred vigorously and 10.6 g (1 eq.) of methanesulfonyl chloride are added at between 20 and 23° C., over 10 minutes. The mixture is maintained for 1 hour at 20-23° C. and is then neutralized very slowly (over 2 hours) to pH 5.5-6 by adding sodium hydrogen carbonate (8.2 g in total). The mixture is maintained for 30 minutes and is then acidified with 5 ml of 36% hydrochloric acid. The salts formed are removed by filtration and the reaction medium is concentrated under vacuum to a residual volume of 35 ml. 100 ml of 1N hydrochloric acid are then added and the mixture is concentrated again to a residual volume of 95 ml in order to remove the residual methanol. The precipitated product (13.3 g, 75.6%) is recovered by filtration and the filtration mother liquors are extracted with 3 times 50 ml of ethyl acetate. Concentrating the ethyl acetate to dryness gives a further 1.9 g (11.6%).
Total yield: 87.2% by weight
m.p.: 157.1° C. (lit. 154.5-155.5° C.)

Example 2

Synthesis of p-benzenesulfonamidophenol (or N-(4-hydroxyphenyl)benzenesulfonamide)

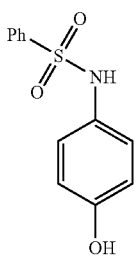

The same procedure as above (Example 1) is followed, starting with 10.9 g (0.1 mol) of p-aminophenol in 40 ml of anhydrous pyridine and 18 g (1 equivalent) of benzenesulfonyl chloride. 14.8 g of p-benzenesulfonamidophenol are obtained.
Mass yield: 59.4% by weight
m.p.: 156° C. (lit. 154.5-155.5° C.)
$^1$H NMR (DMSO) δ 6.6 (d, 2H$_{arom}$), 6.8 (d, 2H$_{arom}$), 7.5 (m, 5H$_{arom}$), 9.3 and 9.7 (2 broad s, OH and NH); $^{13}$C NMR (DMSO) δ 115.4, 124.0, 126.6, 128.9, 132.9 (9-CH$_{arom}$), 128.3 (1-C$_{arom}$—N), 139.5 (1-C$_{arom}$—S), 154.8 (1-C$_{arom}$—O).

Example 3

Synthesis of p-quinone monomethanesulfonimide or N-(4-oxocyclohexa-2,5-dien-1-ylidene)methanesulfonamide) by oxidation of p-methanesulfonamidophenol with K$_2$Cr$_2$O$_7$

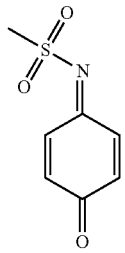

0.8 g (2.72 mmol) of $K_2Cr_2O_7$ is stirred for 1 hour at 20° C. in 20 ml of acetic acid. The dissolution remains partial. 1 g (5.34 mmol) of p-methanesulfonamidophenol is added and the mixture is stirred for 2 hours 30 minutes at 20° C. Next, 40 ml of water are added and the reaction medium is rapidly extracted with 3 times 25 ml of dichloromethane. The organic phases are combined and washed with 25 ml of water. On concentrating to dryness, 0.85 g of product is obtained.

Mass yield: 86% by weight $^1$H NMR (DMSO) δ 3.41 (s, 3H), 6.83 (m, 2H, $CH_{arom}$), 7.17 (m, 1H, $CH_{arom}$), 7.84 (m, 1H, $CH_{arom}$); $^{13}$C NMR (DMSO) δ 42.5 (1-$CH_3$), 129.5, 135.6, 136.0, 139.9 (4-CH), 164.2 (1-C=N), 186.0 (1-C=O).

Synthesis of p-quinone monomethanesulfonimide by oxidation of p-methanesulfonamidophenol with $MnO_2$

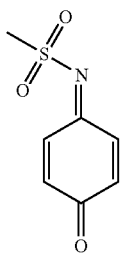

A mixture containing 20 g (0.107 mol) of p-methanesulfonamidophenol, 44 g (4 eq.) of activated 85% $MnO_2$ and 300 ml (15 vol.) of acetic acid is stirred at 25±5° C. for 45 minutes, and the insoluble matter is then filtered off and washed with twice 150 ml of acetic acid. The filtration mother liquors and the washing waters are combined and concentrated under vacuum. The residue is taken up with 300 ml of dichloromethane. The undissolved matter is removed by filtration and washed with 100 ml of dichloromethane. Concentrating the dichloromethane phases under vacuum gives 13.6 g of p-quinone monomethanesulfonimide.

Mass yield: 68.7%.

Melting point in accordance with the literature (134° C.).

The retention time by HPLC analysis is identical to that of p-quinone monomethanesulfonimide obtained via the method of R. Adams et al.

OR

A mixture containing 30 g (0.160 mol) of p-methanesulfonamidophenol, 18 g (1.1 eq.) of activated 85% $MnO_2$ and 450 ml (15 vol.) of acetic acid is stirred at 25±5° C. for 1 hour, and the insoluble matter is then filtered off and washed with four times 200 ml of acetic acid. The filtration mother liquors and the washing waters are combined and concentrated under vacuum. The residue is taken up in a mixture of 600 ml of dichloromethane and 250 ml of water. The phases are separated by settling, the organic phase is retained and the aqueous phase is re-extracted with 150 ml of dichloromethane. The combined dichloromethane phases are concentrated under vacuum and the solid obtained is taken up in 250 ml of ethanol. The product is filtered off and dried under vacuum. 27.06 g of p-quinone monomethanesulfonimide are obtained.

Mass yield: 91.5%.

Melting point in accordance with the literature (134° C.).

The retention time by HPLC analysis is identical to that of p-quinone monomethanesulfonimide obtained via the method of R. Adams et al.

Example 4

Synthesis of ethyl 2-[5-(benzenesulfonamido)-2-hydroxyphenyl]-3-oxo-butanoate

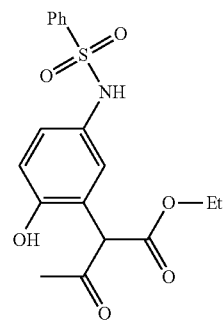

A mixture containing 1 g (3.7 mmol) of p-quinone monobenzenesulfonimide and 0.55 g (1.1 eq.) of ethyl acetoacetate in 20 ml of 1,4-dioxane is stirred at 20±3° C. for 5 minutes, followed by addition of 30 mg of sodium methoxide (powder). The reaction medium is continuously stirred at 20° C. for 30 minutes and then filtered and concentrated under vacuum to remove half of the solvent, and 130 ml of methylcyclohexane are added in portions of 30 to 50 ml alternating with distillation in order to remove the dioxane azeotropically. The oil formed is taken up in 100 ml of ethanol and concentrated to a residual volume of 10 ml. The residue is cooled to 0° C. for 1 hour, and the crystals are filtered off and washed with twice 3 ml of ethanol at 0° C. 0.5 g of crude product is obtained.

Mass yield: 35.6% by weight $^1$H NMR (DMSO) δ 1.15 (t, 3H, $CH_3$), 1.96 (s, 3H, $CH_3$), 4.09 (q, 2H, $CH_2$), 4.98 (s, 1H, CH), 6.73 (d, 1H, $CH_{arom}$), 6.74 (d, 1H, $CH_{arom}$), 6.87 (dd, 1H, $CH_{arom}$), 7.41 to 7.61 (m, 5H, $CH_{arom}$), 9.77, 9.82 (2 broad s, 2H, NH and OH); $^{13}$C NMR (DMSO) δ 13.8 (1-$CH_3$), 28.6 (1-$CH_3$), 57.8 (1-CH), 60.8 (1-$CH_2$), 115.4, 123.7, 123.8 (3-$CH_{arom}$), 120.2, 128.5, 139.2, 152.4 (4-$C_{arom}$), 126.5, 128.9, 132.5 (5-$CH_{arom}$), 168.3, 201.8 (2-C=O).

Example 5

Synthesis of ethyl 5-benzenesulfonamido-2-methyl-benzofuran-3-carboxylate (or ethyl 5-(benzenesulfonamido)-2-methylbenzofuran-3-carboxylate)

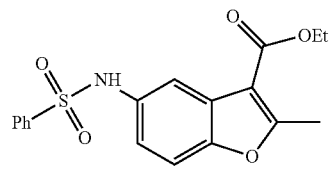 [SMILES: CCOC(=O)c1c(C)oc2ccc(NS(=O)(=O)c3ccccc3)cc12]

0.25 g of the product obtained previously is stirred in 12.5 ml of 20% hydrochloric acid for 3 hours at reflux and then filtered at 0° C. and washed with 4 ml of ice-cold water. 0.24 g of crude ethyl 5-benzenesulfonamido-2-methylbenzofuran-3-carboxylate is obtained.

Mass yield: 100%

$^1$H NMR (DMSO) δ 1.34 (t, 3H, CH$_3$), 2.66 (s, 3H, CH$_3$), 4.29 (q, 2H, CH$_2$), 7.04 (dd, 1H, CH$_{arom}$), 7.46 (d, 1H, CH$_{arom}$), 7.64 (d, 1H, CH$_{arom}$), 7.48 to 7.61 and 7.70 to 7.76 (m, 5H, CH$_{arom}$), 10.3 (S, 1H, NH); $^{13}$C NMR (DMSO) δ 14.0 (2-CH$_3$), 60.0 (1-CH$_2$), 111.3, 113.5, 118.4 (3-CH$_{arom}$), 108.1, 125.9, 133.8, 139.2, 150.0 (5-C$_{arom}$), 126.6, 129.1, 132.7 (5-CH$_{arom}$).

Example 6

Synthesis of ethyl 2-[2-hydroxy-5-(methanesulfonamido)phenyl]-3-oxobutanoate

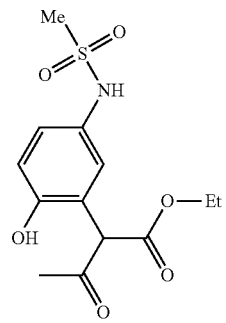 [SMILES: CCOC(=O)C(C(C)=O)c1cc(NS(C)(=O)=O)ccc1O]

The procedure is performed in the same manner as previously in Example 4, with 1 g (5 mmol) of p-quinone monomethanesulfonimide obtained from 1.75 g of substituted p-methanesulfonamidophenol in oil form.

$^1$H NMR (DMSO) δ 1.18 (t, 3H, CH$_3$), 2.13 (s, 3H, CH$_3$), 2.84 (s, 3H, CH$_3$S), 4.12 (q, 2H, CH$_2$), 5.10 (s, 1H, CH), 6.84 (d, 1H, CH$_{arom}$), 6.97 (d, 1H, CH$_{arom}$), 7.03 (dd, 1H, CH$_{arom}$), 9.77, 9.82 (2 broad s, 2H, NH and OH); $^{13}$C NMR (DMSO) δ 13.8 (1-CH$_3$), 28.9 (1-CH$_3$), 38.2 (1-CH$_3$), 58.0 (1-CH), 60.8 (1-CH$_2$), 115.5, 123.4, 123.8 (3-CH$_{arom}$), 120.4, 129.2, 152.4 (3-C$_{arom}$), 154.8 (1-C$_{arom}$—O), 168.4, 201.9 (2-C=O).

Example 7

Synthesis of 5-methanesulfonamido-2-methylbenzofuran-3-carboxylic acid (or 5-(methanesulfonamido)-2-methylbenzofuran-3-carboxylic acid)

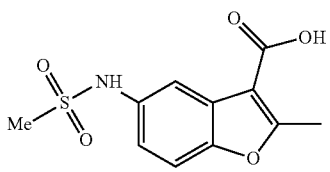 [SMILES: Cc1oc2ccc(NS(C)(=O)=O)cc2c1C(=O)O]

1 g of the product obtained in Example 6 is cyclized in 40 ml of acetone and 25 ml of 36% HCl. The mixture is refluxed for 12 hours and then concentrated under vacuum and the residue is taken up in 10 ml of 10% sodium hydroxide and stirred at 30° C. for 1 hour (saponification of the ester part). The aqueous phase is extracted with 10 ml of DCM and then acidified to pH<4 with 36% HCl solution. The precipitate is filtered off. 0.64 g of crude 5-methanesulfonamido-2-methylbenzofuran-3-carboxylic acid is obtained.

Mass yield: 74.4%

$^1$H NMR (DMSO) δ 2.70 (s, 3H, CH$_3$), 2.91 (s, 3H, CH$_3$S), 7.21 (dd, 1H, CH$_{arom}$), 7.55 (d, 1H, CH$_{arom}$), 7.81 (d, 1H, CH$_{arom}$), 13.04 (s, 1H, NH); $^{13}$C NMR (DMSO) δ 14.1 (1-CH$_3$), 38.5 (1-CH$_3$), 111.2, 113.7, 118.5 (3-CH$_{arom}$), 108.9, 126.7, 134.4, 150.1 (4-C$_{arom}$), 164.0, 164.7 (2-C).

Example 8

Synthesis of methyl 2-[2-hydroxy-5-(methanesulfonamido)phenyl]-3-oxoheptanoate

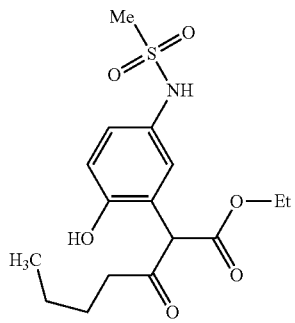 [SMILES: CCCCC(=O)C(C(=O)OCC)c1cc(NS(C)(=O)=O)ccc1O]

A mixture containing 2 g (10.8 mmol) of p-quinone monomethanesulfonimide and 1.88 g (1.1 eq.) of methyl 3-oxoheptanoate in 50 ml of 1,4-dioxane is stirred at 20° C.±3° C., followed by addition of 50 mg of sodium methoxide (powder), and stirring is continued for 30 minutes. The reaction medium is filtered and the residue is taken up in 40 ml of acetone.

$^1$H NMR (DMSO) δ 0.79 (t, 3H, CH$_3$), 1.18 (m, 2H, CH$_2$), 1.42 (quintet, 2H, CH$_2$), 2.49 (m, 2H, CH$_2$), 2.84 (s, 3H, CH$_3$), 3.65 (s, 3H, CH$_3$), 5.16 (s, 3H, CH$_3$), 6.83 (d, 1H, CH$_{arom}$), 6.97 (d, 1H, CH$_{arom}$), 7.03 (dd, 1H, CH$_{arom}$), 9.22, 9.85 (2 broad s, 2H, NH and OH); $^{13}$C NMR (DMSO) δ 13.5 (1-CH$_3$), 21.3 (1-CH$_2$), 25.1 (1-CH$_2$), 38.2 (1-CH$_3$), 40.6 (1-CH$_2$), 52.1 (1-CH and 1-CH$_3$O), 115.5, 123.4, 123.9 (3-CH$_{arom}$), 120.2, 128.8, 152.3 (3-C$_{arom}$), 168.9, 204.0 (2-00).

Example 9

Synthesis of 2-butyl-5-methanesulfonamidobenzofuran-3-carboxylic acid (or 2-butyl-5-(methanesulfonamido)benzofuran-3-carboxylic acid) According to Method I

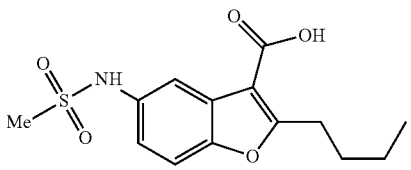 [SMILES: CCCCc1oc2ccc(NS(C)(=O)=O)cc2c1C(=O)O]

70 ml of acetone and 57.5 ml of 36% hydrochloric acid are added to 20 ml of the acetone-based solution obtained after Example 8. This mixture is refluxed for 5 hours and then concentrated under vacuum. The residue is stirred for 1 hour in the presence of 220 ml of 10% sodium hydroxide solution (pH=13-14) and then extracted three times with 10 ml of DCM and finally is precipitated from 36% HCl solution. 1.1 g of crude 2-butyl-5-methanesulfonamidobenzofuran-3-carboxylic acid are obtained.

Yield: 66.4% by weight $^1$H NMR (DMSO) δ 0.90 (t, 3H, CH$_3$), 1.33 (sextet, 2H, CH$_2$), 1.69 (quintet, 2H, CH$_2$), 2.91 (s, 3H, CH$_3$), 3.15 (t, 2H, CH$_2$), 7.56 (d, 1H, CH$_{arom}$), 7.21 (dd, 1H, CH$_{arom}$), 7.83 (d, 1H, CH$_{arom}$), 9.61 (s, 1H, NH); $^{13}$C NMR (DMSO) δ 13.4 (1-CH$_3$), 21.6 (1-CH$_2$), 26.9 (1-CH$_2$), 29.3 (1-CH$_2$), 38.5 (1-CH$_3$), 115.5, 123.4, 123.9 (3-CH$_{arom}$), 108.7, 126.7, 134.3, 150.2 (4-C$_{arom}$), 164.6, 167.4 (1-C—O and 1-C=O).

Synthesis of 2-butyl-5-methanesulfonamidobenzofuran-3-carboxylic acid (or 2-butyl-5-(methanesulfonamido)benzofuran-3-carboxylic acid) According to Method II

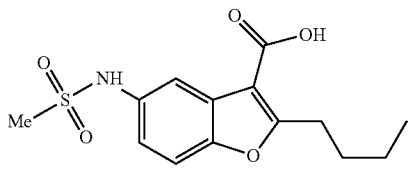

The coupling is performed under the same conditions as previously (Example 8), and, after filtering the reaction medium, the crude product is left in the dioxane to perform the cyclization. Hydrochloric acid is added in the same proportions and the mixture is maintained at a temperature of 50° C. for 1 hour 30 minutes. It is concentrated under vacuum and the residue is taken up in 10% NaOH and stirred at 25° C. for 21 hours, and the product is then precipitated out by adding 36% HCl. 1.5 g of crude 2-butyl-5-methanesulfonamidobenzofuran-3-carboxylic acid are obtained.

Mass yield: 89.2% by weight

Example 10

Synthesis of 2-butyl-5-(methanesulfonamido)benzofuran-3-carbonyl chloride

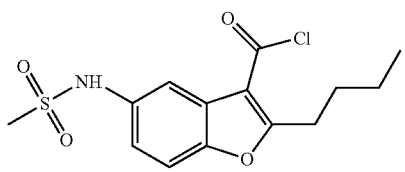 [SMILES: CCCCc1oc2ccc(NS(C)(=O)=O)cc2c1C(=O)Cl]

7 g (22.48 mmol) of 2-butyl-5-methanesulfonamidobenzofuran-3-carboxylic acid are dissolved in 50 g of thionyl chloride and stirred for 3 hours at 20-25° C. and then refluxed for 30 minutes (79° C.). The reaction medium is then concentrated to dryness under reduced pressure and the residue (8.8 g) is taken up in 46.2 g of anhydrous DCE (total mass=55 g).

Preparation of the Sample 2 drops of reaction medium are taken up with stirring and diluted with 1.5 ml of MeOH+0.5 ml of CH$_3$CN.

Column: Xterra RP18 3.5 µm, 100 mm*4.6 mm.

Mobile phase:
A—0.01M KH$_2$PO$_4$ buffer
B—Acetonitrile
Flow rate: 1.0 ml/min.
Gradient:

| Time (min) | % A | % B |
|---|---|---|
| 0 | 80 | 20 |
| 15 | 25 | 75 |
| 25 | 25 | 75 |
| 27 | 80 | 20 |
| 37 | 80 | 20 |

Detector: UV at 226 nm

Injection: 10 µl of product in dioxane/H$_2$O (95/5)

Retention:

Product retention times 2.6 min p-methanesulfonamidophenol 3.4 min p-quinone monomethanesulfonimide 10.6 min dronedarone hydrochloride 11.3 min 2-butyl-5-(methanesulfonamido)benzofuran-3-carbonyl chloride Example 11

Synthesis of N,N-diethyl-N-(phenoxyethyl)amine hydrochloride (or N,N-diethyl-2-phenoxyethanamine)

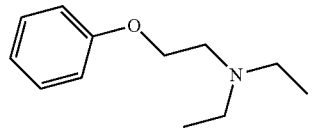

A solution of 108.5 g (0.630 mol; 1.2 eq.) of N-(2-chloroethyl)-N,N-diethylamine hydrochloride in 65 ml of water is added slowly (over about 55 minutes) to a mixture containing 50 g (0.531 mol) of phenol and 46.3 g (1.158 mol; 2.2 eq.) of NaOH in 270 ml of water. The mixture is stirred for 3 hours 30 minutes at 20° C. and then for 45 minutes at 55° C. The phases are separated by settling and the supernatant oil diluted in 100 ml of DCE is washed with (i) 100 ml of 2.5% sodium hydroxide and then (ii) with 100 ml of 5% sodium hydroxide. The product is dried over sodium sulfate and then concentrated. 81.4 g of crude N,N-diethyl-N-(phenoxyethyl)amine are obtained.

Mass yield: 79.3% by weight $^1$H NMR (DMSO) δ 1.08 (t, 6H, 2-CH$_3$), 2.64 (q, 4H, 2-CH$_2$), 2.88 (t, 2H, CH$_2$—N), 4.05 (t, 2H, CH$_2$—O), 6.92 (m, 3H, CH$_{arom}$), 7.27 (m, 2H, CH$_{arom}$); $^{13}$C NMR (DMSO) δ 12.0 (2-CH$_3$), 47.9 (2-CH$_2$—N), 51.8 (1-CH$_2$), 66.5 (1-CH$_2$—O), 114.6, 120.7, 129.4 (5-CH$_{arom}$), 158.9 (1-C$_{arom}$—O).

N,N-Diethyl-N-(phenoxyethyl)amine hydrochloride is formed by dissolving 35 g (0.181 mol) of the preceding N,N-diethyl-N-(phenoxyethyl)amine in 450 ml of anhydrous MTBE, followed by sparging 7 g (0.181 mol) of hydrogen chloride gas into the medium. The precipitate formed is isolated by filtration and dried in a ventilated oven at 55° C. for 3 hours to give 40 g of N,N-diethyl-N-(phenoxyethyl)amine hydrochloride.

Example 12

Synthesis of N,N-dibutyl-N-(3-phenoxypropyl) amine hydrochloride (or dibutyl(3-phenoxypropyl) ammonium chloride)

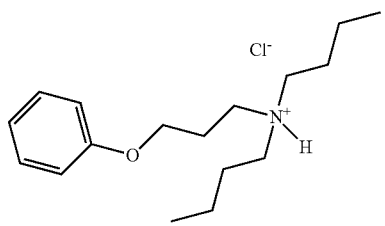 [SMILES: CCCC[NH+](CCCC)CCCOc1ccccc1 ; [Cl-]]

The process is performed in the same manner as previously (Example 13), starting with 138 g (1.466 mol; 1.15 eq.) of phenol, 109.5 g (2.738 mol; 2.15 eq.) of NaOH, 530 ml of distilled water and 308.9 g (1.275 mol; 1 eq.) of N-(3-chloropropyl)-N,N-dibutylamine hydrochloride. The mixture is refluxed for 16 hours. The oil formed is separated out by settling and washed with 500 ml of water and then diluted with 500 ml of MTBE and washed with 500 ml of 2% HCl. The MTBE phase is concentrated under vacuum and the oil is dried by azeotropic distillation with DCM. 307.1 g of the crude derivative N,N-dibutyl-N-(3-phenoxypropyl)amine are obtained.

Mass yield: 91.4% by weight
297.3 g (1.13 mol) of the N,N-dibutyl-N-(3-phenoxypropyl) amine isolated previously are stirred in 600 ml of DCE, and 148.9 g (1.469 mol; 1.3 eq.) of 36% HCl are added, at 20° C. The mixture is stirred for 1 hour at this temperature and dried by azeotropic distillation with DCE until a water content ≤0.01% is obtained, and is then concentrated under vacuum. 363.1 g of N,N-dibutyl-N-(3-phenoxypropyl)amine hydrochloride are obtained.

Titer: 93.7% (Yld 100%).
$^1$H NMR (DMSO) δ 0.93 (t, 6H, 2-CH$_3$), 1.36 (sextet, 4H, 2-CH$_2$), 1.77 (m, 4H, 2-CH$_2$), 2.33 (m, 2H, CH$_2$), 2.98 (m, 4H, 2-CH$_2$—N), 3.19 (m, 2H, CH$_2$—N), 4.04 (t, 2H, CH$_2$—O), 6.82, 6.93, 7.24 (m, 5H, CH$_{arom}$); $^{13}$C NMR (DMSO) δ 13.6 (2-CH$_3$), 20.2 (2-CH$_2$), 23.8 (1-CH$_2$), 25.0 (2-CH$_2$), 50.4 (1-CH$_2$—N), 52.5 (2-CH$_2$—N), 64.7 (1-CH$_2$—O), 114.4, 121.4, 129.6, (5-CH$_{arom}$), 158.1 (1-C$_{arom}$—O).

Example 13

Synthesis of dronedarone coupling by Friedel-Crafts reaction of 2-butyl-5-methanesulfonamidobenzofuran-3-carboxylic acid chloride with N,N-dibutyl-N-(3-phenoxypropyl)amine hydrochloride 7.34 g (22.5 mmol) of N,N-dibutyl-N-(3-phenoxypropyl) amine hydrochloride and 40 g of DCE are introduced into the total amount (55 g) of the preceding reaction medium of Example 10. The mixture is cooled to between 0 and 5° C. and 12 g (4 eq.) of AlCl$_3$ are added. The reaction medium is stirred at 20-25° C. for 4 hours and then hydrolyzed by pouring it into 75 ml of water at between 0 and 5° C. The organic phase is washed twice with 75 ml of water, filtered and then washed again with 75 ml of water and concentrated under reduced pressure. 6.8 g of crude product are obtained.

The crude product is purified by dissolution in 50 ml of DCE and washed with 40 ml of 10% sodium hydroxide and 50 ml of water, and finally the crude product thus obtained is purified by chromatography on silica, eluting with ethyl acetate (90 v)/methanol (10 v). 2.2 g of dronedarone are obtained in a purity of 94.6%.

Mass yield: 16.6% by weight
$^1$H NMR (DMSO) δ 0.83 (t, 3H, CH$_3$), 0.85 (t, 6H, 2-CH$_3$), 1.20 to 1.50 (unresolved complex, 6H, 3-CH$_2$), 1.69 (m, 2H, CH$_2$), 1.90 (m, 2H, CH$_2$), 2.40 (m, 4H, 2-CH$_2$—N), 2.57 (m, 2H, CH$_2$—N), 2.80 (t, 2H, CH$_2$), 2.87 (s, 3H, CH$_3$—S), 4.06 (broad t, 2H, CH$_2$—O), 6.92 (d, 2H, CH$_{arom}$), 7.25, 7.34, 7.39 (m, 3H, CH$_{arom}$), 7.78 (d, 2H, CH$_{arom}$), 12.19 (s, 1H, NH); $^{13}$C NMR (DMSO) δ 13.7 (1-CH$_3$), 14.1 (2-CH$_3$), 20.7 (2-CH$_2$), 26.9, 28.0 (2-CH$_2$), 30.0 (1-CH$_2$), 29.2 (2-CH$_2$), 38.9 (1-CH$_3$—S), 53.9 (2-CH$_2$—N), 50.3 (1-CH$_2$—N), 66.6 (1-CH$_2$—O), 114.3, 131.7 (4-CH$_{arom}$), 111.7, 115.6, 120.2 (3-CH$_{arom}$), 116.8, 128.1, 132.8 (3-C$_{arom}$), 131.3 (1-C$_{arom}$—N), 151.8, 163.3, 165.7 (3-C$_{arom}$—O), 190.4 (1-CO).

Example 14

Synthesis of phenyl 2-butyl-5-methanesulfonamidobenzofuran-3-carboxylate (or phenyl 2-butyl-5-(methanesulfonamido)benzofuran-3-carboxylate)

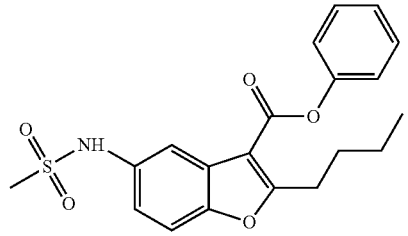 [SMILES: CCCCc1oc2ccc(NS(C)(=O)=O)cc2c1C(=O)Oc1ccccc1]

The following solution is placed in a 250 ml reactor containing the acid chloride of Example 10 in solid residue form: 3.53 g of phenol (1.2 eq.) and 50 ml of CH$_2$Cl$_2$ (anhydrous). The medium dissolves gradually. The addition vessel is rinsed with 50 ml of CH$_2$Cl$_2$ (anhydrous).

The following solution is added to the reaction medium at 30-35° C.: 2.47 g of pyridine (1 eq.), 25 ml of dichloromethane (anhydrous). The reaction medium is extracted with a mixture of 6.3 g of HCl (36%) and 100 ml of H$_2$O (distilled). The mixture is stirred for 15 minutes and the phases are then separated by settling. The organic phase is then washed with: 50 ml of H$_2$O and 30 g of about 3% NaOH. The organic phase is washed again with: 50 ml of H$_2$O and then concentrated, and the following is added to precipitate the product: 100 ml of cyclohexane. The mixture is concentrated under vacuum at 20-25° C. to gradually remove the DCM. The mixture is filtered. 14.4 g of oily residue to be purified are obtained.

Calculated titer (if 100% yield taking into account the organic purity obtained by HPLC)=84%

Same analytical method as for Example 10.

Example 15

Synthesis of N-[2-butyl-3-(4-hydroxybenzoyl)benzofuran-5-yl]methanesulfonamide According to a Fries Reaction

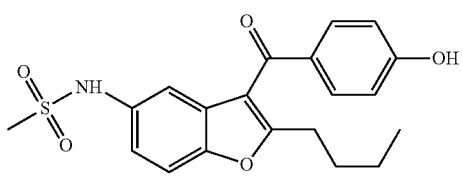 [SMILES: CCCCc1oc2ccc(NS(C)(=O)=O)cc2c1C(=O)c1ccc(O)cc1]

4 g of phenyl 2-butyl-5-methanesulfonamidobenzofuran-3-carboxylate and 40 ml of chlorobenzene are placed in a 100 ml four-necked flask. The mixture is stirred until dissolution is complete, and 4.1 g of $AlCl_3$ (4 equivalents) are then added and the mixture is heated at 95° C. for 17 hours. The reaction medium is cooled to 20-25° C. and diluted with: 40 ml of $CH_2Cl_2$. The mixture obtained is hydrolyzed by pouring it into 80 ml of $H_2O$, without exceeding 35° C. The resulting mixture is stirred at 20-25° C. until the gums have disappeared, and the phases are then separated by settling. The organic phase is washed once again with 80 ml of $H_2O$. 50 ml of $H_2O$ are added to the organic phase and the pH is adjusted to 12.5 by addition of: 2.3 g of NaOH (30%). The mixture is stirred at 20-25° C. and the phases are then separated by settling.

The aqueous phase is brought to acidic pH by addition of 1.6 g of HCl (36%), 40 ml of $CH_2Cl_2$ are added, the mixture is stirred and the phases are then separated by settling.

After concentrating the organic phase, 2.3 g of solid residue are obtained and are purified by flash chromatography to give 1.09 g of the desired intermediate (para isomer).

Yield=27.3%

Same analytical method as for Example 10.

The invention claimed is:

1. A process for synthesizing a keto benzofuran derivative, in acid form (i), in base form (ii), in the form of an addition salt with an acid or a base (iii), in hydrate form (iv) or in solvate form (v), advantageously dronedarone or the hydrochloride salt thereof, said keto benzofuran derivative being of formula (I) below:

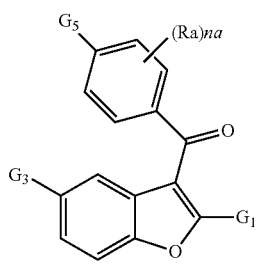

in which G1 represents a linear or branched alkyl (i), haloalkyl (ii), cycloalkyl (iii), substituted or unsubstituted aryl (iv), alkene (v) or alkyne (vi) group, G3 represents (i) a group —NHSO2Rc or (ii) a group —NHRc, in which Rc represents (a) a linear or branched alkyl group, (b) a cycloalkyl group or (c) a substituted or unsubstituted aryl group, G5 represents a halogen atom or a group —ORb in which Rb represents a hydrogen atom, an alkyl, haloalkyl, aryl, arylalkyl, heteroaryl, cycloalkyl or heterocycloalkyl group or an -alkylene-aminoalkyl group, Ra represents a substituent chosen from a hydrogen atom, halogen atoms and alkyl, haloalkyl, alkoxy and alkoxyalkyl groups, na is an index equal to 0, 1, 2, 3 or 4, said process comprising a Fries rearrangement reaction, said reaction taking place starting with an intermediate of formula (II)

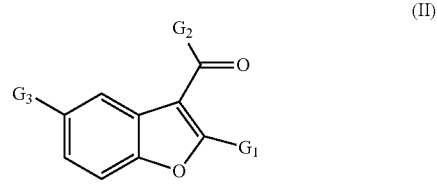

in which the group G2 is

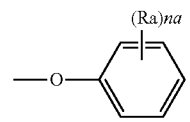

in which the phenyl is optionally substituted in the ortho and/or meta position, but never in the para position.

2. The process of claim 1, further comprising preparing by dehydrating a compound of formula (IX):

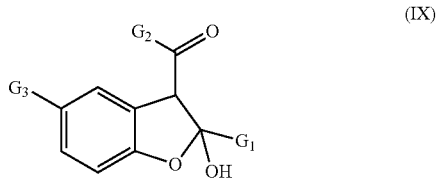

to form the compound of formula (II).

3. The process of claim 2, further comprising cyclization reacting a compound of formula (VIII):

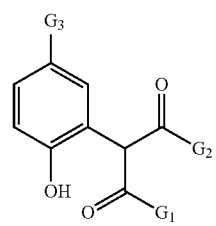

to form a compound of formula (IX).

4. The process of claim 1, characterized in that wherein the compound of formula (I) is the compound of formula (12):

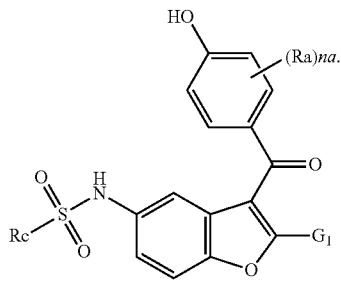
(12)

5. A compound in base form, or in the form of a pharmaceutically acceptable addition salt with organic or mineral acids, having one of the following formulas:

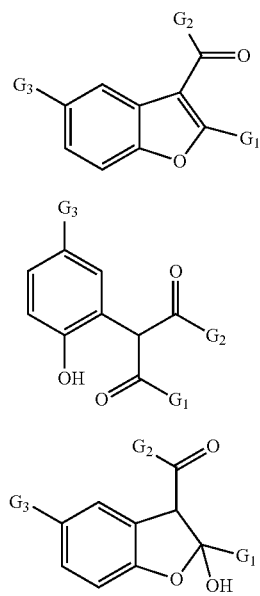

(II)

(VIII)

(IX)

in which G1 and G3 are as defined for the keto benzofuran of formula (I) as claimed in claim 1 and in which the group G2 is chosen from the following groups

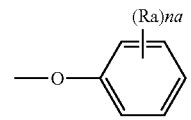

in which the phenyl is optionally substituted in the ortho and/or meta position, but never in the para position, with said radical Ra, Ra represents a substituent chosen from a hydrogen atom, halogen atoms and alkyl, haloalkyl, alkoxy and alkoxyalkyl groups, na is an index equal to 0, 1, 2, 3 or 4.

6. A compound of formula (12), in base form, or in the form of pharmaceutically acceptable addition salts with organic or mineral acids, said compound having the following formula:

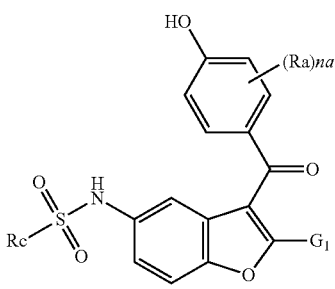
(12)

In which, G1 represents a linear or branched alkyl (i), haloalkyl (ii), cycloalkyl (iii), substituted or unsubstituted aryl (iv), alkene (v) or alkyne (vi) group, Rc represents (a) a linear or branched alkyl group, (b) a cycloalkyl group or (c) a substituted or unsubstituted aryl group, Ra represents a substituent chosen from a hydrogen atom, halogen atoms and alkyl, haloalkyl, alkoxy and alkoxyalkyl groups, na is an index equal to 0, 1, 2, 3 or 4.

7. The process according to claim 1, wherein said keto benzofuran derivative is dronedarone or the hydrochloride salt thereof.

* * * * *